(12) United States Patent
Binner et al.

(10) Patent No.: US 8,864,640 B2
(45) Date of Patent: Oct. 21, 2014

(54) METHODS OF PACKAGING INTRAVAGINAL DEVICE

(75) Inventors: Curt Binner, Furlong, PA (US); Samuel C. Carasso, Milltown, NJ (US); David J. Chase, Somerville, NJ (US); Erin Marsee, Nicholasville, KY (US); Tara Glasgow, Glen Ellyn, IL (US); David L. Kimball, Flemington, NJ (US); Julia K. Iris, North Wales, PA (US); Tony C. Ng, East Brunswick, NJ (US)

(73) Assignee: McNeil-PPC, Inc., Skillman, NJ (US)

( * ) Notice: Subject to any disclaimer, the term of this patent is extended or adjusted under 35 U.S.C. 154(b) by 2327 days.

(21) Appl. No.: 11/663,137

(22) PCT Filed: May 16, 2005

(86) PCT No.: PCT/US2005/018002
§ 371 (c)(1),
(2), (4) Date: Jun. 18, 2009

(87) PCT Pub. No.: WO2005/112862
PCT Pub. Date: Dec. 1, 2005

(65) Prior Publication Data
US 2009/0260205 A1 Oct. 22, 2009

Related U.S. Application Data

(63) Continuation-in-part of application No. 10/847,951, filed on May 14, 2004, now Pat. No. 8,247,642, and a continuation-in-part of application No. 10/847,952, filed on May 14, 2004, now Pat. No. 8,653,322.

(60) Provisional application No. 60/572,054, filed on May 14, 2004, provisional application No. 60/572,055, filed on May 14, 2004.

(51) Int. Cl.
*A61F 13/20* (2006.01)
*A61F 13/22* (2006.01)
*B31F 1/00* (2006.01)
*A61F 13/551* (2006.01)

(52) U.S. Cl.
CPC ............ *B31F 1/0003* (2013.01); *A61F 13/2065* (2013.01); *A61F 13/206* (2013.01); *A61F 13/55175* (2013.01)
USPC ............................................. 493/454; 28/118

(58) Field of Classification Search
CPC ............ A61F 13/2082; A61F 13/2085; A61F 13/2088; A61F 13/2051; A61F 13/206; A61F 13/2068; A61F 13/2065; A61F 13/55175
USPC ............ 493/250, 405, 426, 454; 28/118, 120, 28/121; 604/385.17
See application file for complete search history.

(56) References Cited

U.S. PATENT DOCUMENTS

| 398,015 | A | 2/1889 | Williams |
| 732,729 | A | 7/1903 | Dowling |

(Continued)

FOREIGN PATENT DOCUMENTS

| AU | 748284 B1 | 2/2000 |
| CA | 2293599 A1 | 6/2001 |

(Continued)

OTHER PUBLICATIONS

In the U.S. Appl. No. 11/661,535 the non-final office action dated Mar. 2, 2012.

(Continued)

*Primary Examiner* — Stephen F Gerrity

(57) ABSTRACT

A method of folding a plurality of flexible elements about a central fluid storage element includes of urging an intravaginal device into a folding device; imparting relative rotation between at least a portion of the folding device and the intravaginal device; and contacting the plurality of flexible extensions with the folding device. Wherein the intravaginal device includes a fluid storage element and a plurality of flexible extensions extending therefrom, and the flexible extensions are folded about the fluid storage element in a uniform direction. Alternatively, in place of relative rotation, the flexible extensions are folded by means of guide rails of the folding device. Several apparatus may be employed in this and related methods.

17 Claims, 10 Drawing Sheets

(56) References Cited

U.S. PATENT DOCUMENTS

| | | | |
|---|---|---|---|
| 735,729 A | 8/1903 | Dowing | |
| 867,176 A | 9/1907 | Warwick | |
| 1,731,665 A | 10/1929 | Huebsch | |
| 1,926,900 A | 9/1933 | Hasse et al. | |
| 1,941,717 A | 1/1934 | Rabell | |
| 2,099,931 A | 11/1937 | Fourness | |
| 2,188,923 A | 2/1940 | Robinson | |
| 2,265,636 A | 12/1941 | Eaton | |
| 2,301,106 A | 11/1942 | Brown | |
| 2,306,406 A | 12/1942 | Robinson | |
| 2,394,219 A | 2/1946 | Vachon | |
| 2,412,861 A | 12/1946 | Beadle et al. | |
| 2,425,004 A | 8/1947 | Rabell | |
| 2,458,685 A * | 1/1949 | Crockford | 28/119 |
| 2,464,310 A | 3/1949 | Harwoord | |
| 2,613,670 A | 10/1952 | Sokolik | |
| 2,624,993 A | 1/1953 | Robertson | |
| 2,830,417 A | 4/1958 | Ullman et al. | |
| RE24,666 E | 7/1959 | Draghi | |
| 3,007,377 A | 11/1961 | Muller | |
| 3,055,369 A | 9/1962 | Graham, Jr. | |
| 3,058,469 A | 10/1962 | Crockford | |
| 3,135,262 A | 6/1964 | Kobler et al. | |
| 3,138,159 A | 6/1964 | Schmidt | |
| 3,340,874 A | 9/1967 | Burgeni | |
| 3,422,496 A | 1/1969 | Wolff | |
| 3,431,909 A | 3/1969 | Krusko | |
| 3,512,528 A | 5/1970 | Whitehead et al. | |
| 3,572,341 A | 3/1971 | Glassman | |
| 3,610,243 A | 10/1971 | Jones, Sr. | |
| 3,618,605 A | 11/1971 | Glassman | |
| 3,643,661 A | 2/1972 | Crockford | |
| 3,661,154 A | 5/1972 | Torr | |
| 3,706,311 A | 12/1972 | Kokx et al. | |
| 3,710,793 A | 1/1973 | Glassman | |
| 3,731,687 A | 5/1973 | Glassman | |
| 3,732,866 A | 5/1973 | Accavallo | |
| 3,762,413 A | 10/1973 | Hanke | |
| 3,811,445 A | 5/1974 | Dostal | |
| 3,834,389 A | 9/1974 | Dulle | |
| 3,845,766 A | 11/1974 | Zoller | |
| 3,851,440 A | 12/1974 | Horsky | |
| 3,929,135 A | 12/1975 | Thompson | |
| RE28,674 E | 1/1976 | Guyette | |
| 3,971,378 A | 7/1976 | Krantz | |
| 3,983,875 A | 10/1976 | Truman | |
| 3,986,511 A | 10/1976 | Olofsson et al. | |
| 4,109,354 A * | 8/1978 | Ronc | 28/119 |
| 4,211,225 A | 7/1980 | Sibalis | |
| 4,212,301 A | 7/1980 | Johnson | |
| 4,335,720 A | 6/1982 | Glassman | |
| 4,341,214 A | 7/1982 | Fries et al. | |
| 4,342,314 A | 8/1982 | Radel et al. | |
| 4,351,339 A | 9/1982 | Sneider et al. | |
| 4,359,357 A | 11/1982 | Fries et al. | |
| 4,372,312 A | 2/1983 | Fendler et al. | |
| 4,373,529 A | 2/1983 | Lilaonitkul et al. | |
| 4,381,326 A | 4/1983 | Keily | |
| 4,508,256 A | 4/1985 | Radel et al. | |
| 4,510,735 A | 4/1985 | Cillario | |
| 4,525,983 A | 7/1985 | Libow | |
| 4,543,098 A | 9/1985 | Wolfe et al. | |
| 4,661,101 A | 4/1987 | Sustmann | |
| 4,675,217 A | 6/1987 | Forsman | |
| 4,685,178 A | 8/1987 | Nakanishi | |
| 4,710,186 A | 12/1987 | DeRossett et al. | |
| 4,816,100 A | 3/1989 | Friese | |
| 4,863,450 A * | 9/1989 | Friese | 604/370 |
| 5,004,467 A | 4/1991 | Hinzmann et al. | |
| 5,165,152 A * | 11/1992 | Kramer et al. | 28/118 |
| 5,180,620 A | 1/1993 | Mende | |
| 5,273,596 A | 12/1993 | Nekirk | |
| 5,295,984 A | 3/1994 | Contente et al. | |
| 5,387,209 A | 2/1995 | Yamamoto et al. | |
| 5,403,300 A | 4/1995 | Howarth | |
| 5,458,835 A | 10/1995 | Wilkes et al. | |
| 5,498,252 A | 3/1996 | Silber | |
| 5,500,270 A | 3/1996 | Langdon et al. | |
| 5,536,555 A | 7/1996 | Zelazoski et al. | |
| 5,545,155 A | 8/1996 | Hseih et al. | |
| 5,567,376 A | 10/1996 | Turi et al. | |
| 5,659,934 A | 8/1997 | Jessup et al. | |
| 5,688,260 A | 11/1997 | Blanton et al. | |
| 5,759,569 A | 6/1998 | Hird et al. | |
| 5,782,063 A | 7/1998 | Boriani et al. | |
| 5,802,806 A | 9/1998 | Scaliti | |
| 5,817,077 A | 10/1998 | Foley et al. | |
| 5,909,884 A * | 6/1999 | Schwankhart | 28/118 |
| 5,911,712 A | 6/1999 | Leutwyler et al. | |
| 5,928,184 A | 7/1999 | Etheredge et al. | |
| 5,928,452 A | 7/1999 | McFall et al. | |
| 5,972,505 A | 10/1999 | Phillips et al. | |
| 6,177,606 B1 | 1/2001 | Etheredge et al. | |
| 6,177,608 B1 | 1/2001 | Weinstrauch | |
| 6,183,436 B1 | 2/2001 | Korteweg et al. | |
| 6,191,341 B1 | 2/2001 | Shippert | |
| 6,206,867 B1 | 3/2001 | Osborn et al. | |
| 6,299,573 B1 | 10/2001 | Hull et al. | |
| 6,310,269 B1 | 10/2001 | Friese et al. | |
| 6,358,235 B1 | 3/2002 | Osborn et al. | |
| 6,433,246 B1 | 8/2002 | Nguyen et al. | |
| 6,436,328 B1 | 8/2002 | DiPalma | |
| 6,465,713 B1 | 10/2002 | Gell et al. | |
| 6,479,130 B1 | 11/2002 | Takai et al. | |
| 6,479,728 B1 | 11/2002 | DiPalma | |
| 6,554,814 B1 | 4/2003 | Agyapont et al. | |
| 6,558,362 B1 | 5/2003 | Chaffringeon | |
| 6,570,055 B2 | 5/2003 | Yang et al. | |
| 6,595,974 B1 | 7/2003 | Pauley et al. | |
| 6,635,800 B2 | 10/2003 | Jackson et al. | |
| 6,719,743 B1 | 4/2004 | Wada | |
| 6,840,927 B2 | 1/2005 | Hasse et al. | |
| 6,860,874 B2 | 3/2005 | Gubernick et al. | |
| 7,101,358 B2 | 9/2006 | Domeier et al. | |
| 7,112,192 B2 | 9/2006 | Hasse et al. | |
| 7,160,279 B2 | 1/2007 | Pauley et al. | |
| 7,172,801 B2 | 2/2007 | Hoying et al. | |
| 7,179,952 B2 | 2/2007 | Vukos et al. | |
| 7,335,194 B2 | 2/2008 | Wada | |
| 7,601,415 B2 | 10/2009 | Cree et al. | |
| 7,618,403 B2 | 11/2009 | Carasso et al. | |
| 7,845,380 B2 * | 12/2010 | Binner et al. | 156/484 |
| 7,861,494 B2 * | 1/2011 | Binner | 53/223 |
| 8,028,500 B2 * | 10/2011 | Binner | 53/223 |
| 8,057,453 B2 | 11/2011 | Chase et al. | |
| 8,231,753 B2 * | 7/2012 | Binner et al. | 156/227 |
| 8,353,890 B2 * | 1/2013 | Schoelling | 28/118 |
| 2002/0012373 A1 | 1/2002 | Yokozeki et al. | |
| 2002/0026177 A1 | 2/2002 | Lochte et al. | |
| 2002/0133135 A1 | 9/2002 | Gell et al. | |
| 2002/0138035 A1 | 9/2002 | Huli et al. | |
| 2003/0093049 A1 | 5/2003 | Johnson et al. | |
| 2003/0097106 A1 | 5/2003 | Hasse et al. | |
| 2003/0097108 A1 | 5/2003 | Hasse et al. | |
| 2003/0105444 A1 | 6/2003 | Lochte et al. | |
| 2003/0135180 A1 | 7/2003 | Nguyen et al. | |
| 2003/0149392 A1 | 8/2003 | Arnould | |
| 2003/0149416 A1 | 8/2003 | Cole et al. | |
| 2003/0208180 A1 | 11/2003 | Fuchs et al. | |
| 2003/0229328 A1 | 12/2003 | Costa | |
| 2004/0127879 A1 | 7/2004 | Pauley et al. | |
| 2004/0147896 A1 | 7/2004 | Mizutani et al. | |
| 2005/0049566 A1 | 3/2005 | Vukos et al. | |
| 2005/0096620 A1 * | 5/2005 | Awolin et al. | 604/385.18 |
| 2005/0256482 A1 | 11/2005 | Minoguchi et al. | |
| 2005/0256484 A1 | 11/2005 | Chase et al. | |
| 2005/0256485 A1 | 11/2005 | Carasso et al. | |
| 2005/0256486 A1 | 11/2005 | Carasso et al. | |
| 2005/0256511 A1 | 11/2005 | Chase et al. | |
| 2005/0277904 A1 | 12/2005 | Chase et al. | |
| 2005/0283128 A1 | 12/2005 | Chase et al. | |
| 2006/0004338 A1 | 1/2006 | Torkidsen et al. | |
| 2006/0217677 A1 | 9/2006 | Chase et al. | |
| 2006/0235361 A1 | 10/2006 | Agyapong et al. | |

(56) References Cited

U.S. PATENT DOCUMENTS

| | | |
|---|---|---|
| 2007/0010388 A1 | 1/2007 | Binner |
| 2007/0049893 A1 | 3/2007 | Binner et al. |
| 2007/0129698 A1 | 6/2007 | Vukos et al. |
| 2007/0282289 A1 | 12/2007 | Glasgow |
| 2008/0255495 A1 | 10/2008 | Danyi |
| 2009/0171310 A1 | 7/2009 | Carasso et al. |
| 2009/0177173 A1 | 7/2009 | Chase et al. |
| 2010/0069866 A1 | 3/2010 | Binner et al. |
| 2010/0168645 A1 | 7/2010 | Binner et al. |
| 2010/0170069 A1 | 7/2010 | Binner |
| 2010/0192339 A1 | 8/2010 | Binner et al. |
| 2012/0227228 A1* | 9/2012 | Schoelling ............... 28/118 |

FOREIGN PATENT DOCUMENTS

| | | |
|---|---|---|
| EP | 1108408 A | 6/2001 |
| GB | 2292526 A | 2/1996 |
| JP | 48020395 A | 3/1973 |
| JP | 52020799 U | 2/1977 |
| JP | 53163894 U | 12/1978 |
| JP | 56090225 U | 7/1981 |
| JP | 60171044 A | 9/1985 |
| JP | 62155835 U | 10/1987 |
| JP | 3198850 A | 8/1991 |
| JP | 04120734 U | 10/1992 |
| JP | 59528 U | 2/1993 |
| JP | 9510374 T | 10/1997 |
| JP | 2002508216 T | 3/2002 |
| JP | 2004508892 T | 3/2004 |
| WO | WO 83/03537 A | 10/1983 |
| WO | WO 95/24877 A | 9/1995 |
| WO | WO 96/00552 A1 | 1/1996 |
| WO | WO 97/09017 A1 | 3/1997 |
| WO | WO 99/00063 A1 | 1/1999 |
| WO | WO 99/00096 A1 | 1/1999 |
| WO | WO 99/30659 A | 6/1999 |
| WO | WO 00/61052 A | 10/2000 |
| WO | WO 00/63487 A | 10/2000 |
| WO | WO 01/01906 A1 | 1/2001 |
| WO | WO 02/24133 A | 3/2002 |
| WO | WO 02/058609 A | 8/2002 |
| WO | WO 02/076357 A | 10/2002 |
| WO | WO 2005/112856 A | 12/2005 |

OTHER PUBLICATIONS

In the U.S. Appl. No. 13/343,276 the non-final office action dated Mar. 14, 2012.
In the U.S. Appl. No. 11/443,917 the Notice of Allowance dated Mar. 13, 2012.
In the U.S. Appl. No. 11/661,535 the Non-final Office Action dated Oct. 5, 2011.
In the U.S. Appl. No. 11/444,792, US Patent 7,845,380, the Notice of Allowance dated Dec. 4, 2008.
In the U.S. Appl. No. 11/444,792, US Patent 7,845,380, the Notice of Allowance dated Apr. 3, 2009.
In the U.S. Appl. No. 11/444,792, US Patent 7,845,380, the Notice of Allowance dated Dec. 24, 2009.
In the U.S. Appl. No. 11/444,792, US Patent 7,845,380, the Notice of Allowance dated Oct. 1, 2010.
In the U.S. Appl. No. 11/444,792, US Patent 7,845,380, the Notice of Allowance dated Oct. 19, 2010.
In the U.S. Appl. No. 11/478,944, US Patent 7,861,494, the Notice of Allowance dated Oct. 31, 2008.
In the U.S. Appl. No. 11/478,944, US Patent 7,861,494, the Notice of Allowance dated Feb. 24, 2009.
In the U.S. Appl. No. 11/478,944, US Patent 7,861,494, the Notice of Allowance dated Apr. 30, 2009.
In the U.S. Appl. No. 11/478,944, US Patent 7,861,494, the Notice of Allowance dated Jan. 13, 2010.
In the U.S. Appl. No. 11/478,944, US Patent 7,861,494, the Notice of Allowance dated Nov. 15, 2010.
In the U.S. Appl. No. 12/722,681—no official actions received yet.
In the U.S. Appl. No. 12/722,699 the Non-final Office Action dated Aug. 18, 2011.
In the U.S. Appl. No. 12/724,739, US Patent 8,028,500, the Notice of Allowance dated Aug. 9, 2011.
In the U.S. Appl. No. 10/847,951, the communication dated Apr. 5, 2012.
In the U.S. Appl. No. 10/847,951, the Notice of Allowance dated May 25, 2012.
In the U.S. Appl. No. 10/847,952, the Notice of Allowance dated May 4, 2012.
In the U.S. Appl. No. 12/722,699 the Notice of Allowance dated Jun. 21, 2012.
In the U.S. Appl. No. 12/722,681 the Non-final Rejection dated Jul. 13, 2012.
In the U.S. Appl. No. 12/138,009, no official actions received Abandoned.
In the U.S. Appl. No. 12/402,867 the Non-final Office Action dated Sep. 10, 2010.
In the U.S. Appl. No. 12/402,867 the Final Office Action dated Feb. 22, 2011.
In the U.S. Appl. No. 10/847,952 the Non-final Office Action dated Nov. 25, 2005.
In the U.S. Appl. No. 10/847,952 the Restriction Requirement dated Aug. 15, 2006.
In the U.S. Appl. No. 10/847,952 the Final Office Action dated Nov. 26, 2007.
In the U.S. Appl. No. 10/847,952 the Non-final Office Action dated Jun. 18, 2008.
In the U.S. Appl. No. 10/847,952 the Final Office Action dated May 29, 2009.
In the U.S. Appl. No. 10/847,952 the Examiners Answer to Appeal Brief dated Mar. 4, 2010.
In the U.S. Appl. No. 10/847,952 the BPAI Decision—Examiner Reversed dated Jan. 24, 2012.
In the U.S. Appl. No. 10/847,952 the Non-Final Office Action dated Feb. 6, 2012.
In the U.S. Appl. No. 10/882,913, Patent 7,618,403, the Non-final Office Action dated Nov. 28, 2005.
In the U.S. Appl. No. 10/882,913, Patent 7,618,403, the Final Office Action dated Dec. 31, 2007.
In the U.S. Appl. No. 10/882,913, Patent 7,618,403, the Non-final Office Action dated Oct. 29, 2008.
In the U.S. Appl. No. 10/882,913, Patent 7,618,403, the Notice of Allowance dated May 29, 2009.
In the U.S. Appl. No. 12/396,024 the Restriction Requirement dated Sep. 21, 2010.
In the U.S. Appl. No. 12/396,024 the Non-final Office Action dated Jan. 26, 2011.
In the U.S. Appl. No. 12/396,024 the Final Office Action dated Jul. 21, 2011.
In the U.S. Appl. No. 12/847,951 the Non-final Office Action dated Nov. 15, 2005.
In the U.S. Appl. No. 12/847,951 the Restriction Requirement dated Aug. 4, 2006.
In the U.S. Appl. No. 12/847,951 the Final Office Action dated Nov. 17, 2006.
In the U.S. Appl. No. 12/847,951 the Advisory Action dated Apr. 17, 2007.
In the U.S. Appl. No. 12/847,951 the Non-final Office Action dated Jan. 2, 2009.
In the U.S. Appl. No. 12/847,951 the Final Office Action dated Jul. 7, 2009.
In the U.S. Appl. No. 12/847,951 the Advisory Action dated Nov. 6, 2009.
In the U.S. Appl. No. 12/847,951 the Examiners Answer to Appeal Brief dated Mar. 18, 2010.
In the U.S. Appl. No. 12/847,951 the BPAI Decision-Examiner Affirmed in Part dated Jan. 19, 2012.
In the U.S. Appl. No. 13/343,272, no official actions received yet.
In the U.S. Appl. No. 13/343,276, no official actions received yet.
In the U.S. Appl. No. 11/661,535 the Restriction Requirement dated Jul. 21, 2011.

(56) References Cited

OTHER PUBLICATIONS

In the U.S. Appl. No. 11/444,792, Patent 7,845,380, the Restriction Requirement dated Jun. 25, 2008.
In the U.S. Appl. No. 11/478,944, Patent 7,861,494, the Restriction Requirement dated Aug. 1, 2008.
In the U.S. Appl. No. 12/722,699 the Notice of Allowance dated Jan. 17, 2012.
In the U.S. Appl. No. 10/848,257, the Non-final Office Action dated Nov. 17, 2005 Abandoned.
In the U.S. Appl. No. 10/848,257, the Restriction Requirement dated Aug. 2, 2006, Abandoned.
In the U.S. Appl. No. 10/848,257, the Final Office Action dated Nov. 2, 2006 Abandoned.
In the U.S. Appl. No. 10/848,257, the Non-final Office Action dated Sep. 13, 2007 Abandoned.
In the U.S. Appl. No. 10/848,257, the Final Office Action dated Aug. 19, 2008 Abandoned.
In the U.S. Appl. No. 11/762,517, no official actions received Abandoned.
In the U.S. Appl. No. 12/051,562 the Restriction Requirement dated Dec. 31, 2009.
In the U.S. Appl. No. 12/051,562 the Non-final Office Action dated Mar. 29, 2010.
In the U.S. Appl. No. 12/051,562 the Final Office Action dated Sep. 14, 2010.
In the U.S. Appl. No. 11/443,918, Patent 8,057,453, the Restriction Requirement dated Sep. 3, 2008.
In the U.S. Appl. No. 11/443,918, Patent 8,057,453, the Non-final Office Action dated Apr. 8, 2009.
In the U.S. Appl. No. 11/443,918, Patent 8,057,453, the Final Office Action dated Oct. 30, 2009.
In the U.S. Appl. No. 11/443,918, Patent 8,057,453, the Final Office Action dated Mar. 31, 2010.
In the U.S. Appl. No. 11/443,918, Patent 8,057,453, the Non-final Office Action dated Aug. 16, 2010.
In the U.S. Appl. No. 11/443,918, Patent 8,057,453, the Final Office Action dated Jan. 26, 2011.
In the U.S. Appl. No. 11/443,918, Patent 8,057,453, the Notice of Allowance dated Jul. 13, 2011.
In the U.S. Appl. No. 11/443,918, Patent 8,057,453, the Notice of Allowance dated Sep. 19, 2011.
In the U.S. Appl. No. 13/212,670, no official actions received yet.
In the U.S. Appl. No. 10/848,208 the Non-final Office Action dated Nov. 8, 2005 Abandoned.
In the U.S. Appl. No. 11/443,917 the Restriction Requirement dated Sep. 4, 2008.
In the U.S. Appl. No. 11/443,917 the Non-final Office Action dated Feb. 19, 2009.
In the U.S. Appl. No. 11/443,917 the Final Office Action dated Nov. 6, 2009.
In the U.S. Appl. No. 11/443,917 the Non-final Office Action dated Jun. 17, 2010.
In the U.S. Appl. No. 11/443,917 the Final Office Action dated Dec. 6, 2010.
In the U.S. Appl. No. 11/443,917 the Non-final Office Action dated Apr. 21, 2011.
In the U.S. Appl. No. 11/443,917 the Final Office Action dated Oct. 17, 2011.
In the U.S. Appl. No. 10/848,347 the Non-final Office Action dated Nov. 8, 2005 Abandoned.
In the U.S. Appl. No. 11/661,535 the Final Rejection dated Aug. 14, 2012.
In the U.S. Appl. No. 12/722,681 the Final Rejection dated Jan. 4, 2013.
In the U.S. Appl. No. 12/051,562 the Non-Final Rejection dated Jan. 4, 2013.
In the U.S. Appl. No. 11/661,535 the Notice of Allowance dated Apr. 17, 2013.
U.S. Appl. No. 12/051,562 the Final Office Action dated Jun. 26, 2013.
U.S. Appl. No. 13/212,670 the Notice of Allowance dated Jul. 1, 2013.
U.S. Appl. No. 13/444,903 the non-final rejection dated Jul. 25, 2013.
U.S. Appl. No. 13/212,670 the Notice of Allowance dated Aug. 5, 2013.
U.S. Appl. No. 12/402,867 the Notice of Allowance dated Aug. 20, 2013.
U.S. Appl. No. 13/772,569 the Non-Final Rejection dated Sep. 24, 2013.
U.S. Appl. No. 13/772,585 the Non-Final Rejection dated Sep. 9, 2013.
U.S. Appl. No. 12/051,562 the Non-Final Rejection dated Oct. 22, 2013.
U.S. Appl. No. 12/402,867 the Notice of Allowance dated Nov. 6, 2013.
U.S. Appl. No. 12/396,024 the non-final rejection dated Nov. 15, 2013.
U.S. Appl. No. 13/772,524 the non-final rejection dated Nov. 25, 2013.
U.S. Appl. No. 13/772,544 the non-final rejection dated Nov. 25, 2013.
U.S. Appl. No. 10/847,952 the Notice of Allowance dated Dec. 6, 2013.
U.S. Appl. No. 12/722,681 the Notice of Allowance dated Dec. 13, 2013.
U.S. Appl. No. 13/772,569 the Final Rejection dated Feb. 11, 2014.
U.S. Appl. No. 13/772,585 the Final Rejection dated Feb. 11, 2014.
U.S. Appl. No. 12/722,681 the Notice of Allowance dated Feb. 14, 2014.
U.S. Appl. No. 12/396,024 the Final Rejection dated Apr. 10, 2014.
U.S. Appl. No. 13/772,524 the Final Rejection dated Apr. 10, 2014.
U.S. Appl. No. 13/772,544 the Final Rejection dated Apr. 21, 2014.
U.S. Appl. No. 11/663,137 the Notice of Allowance dated Aug. 7, 2014.

* cited by examiner

Fig. 3a
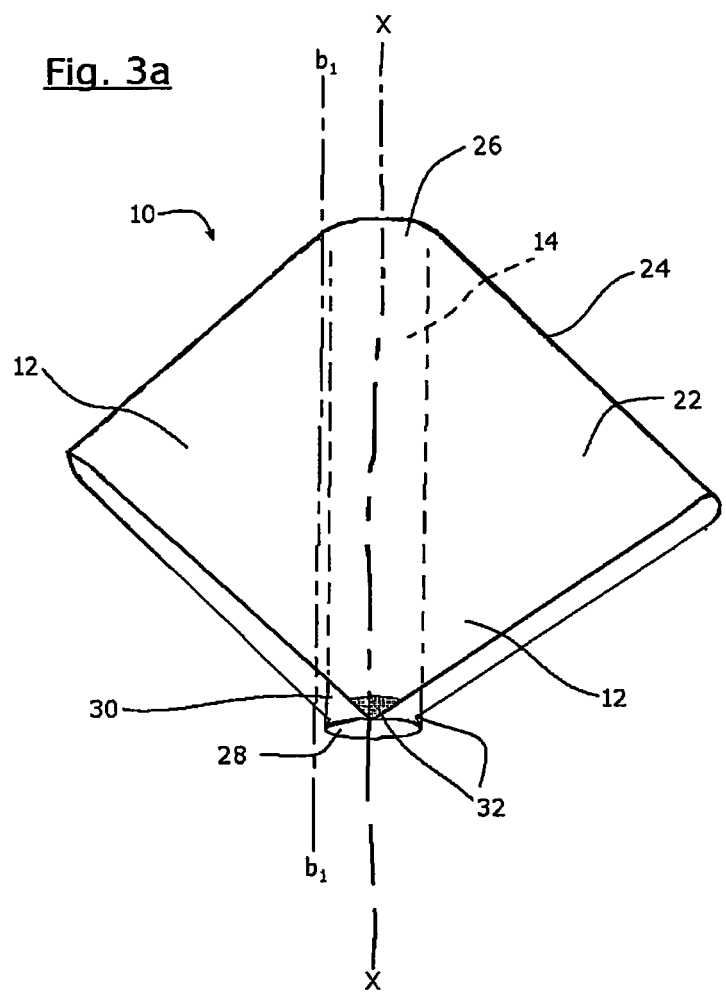
Fig. 3b
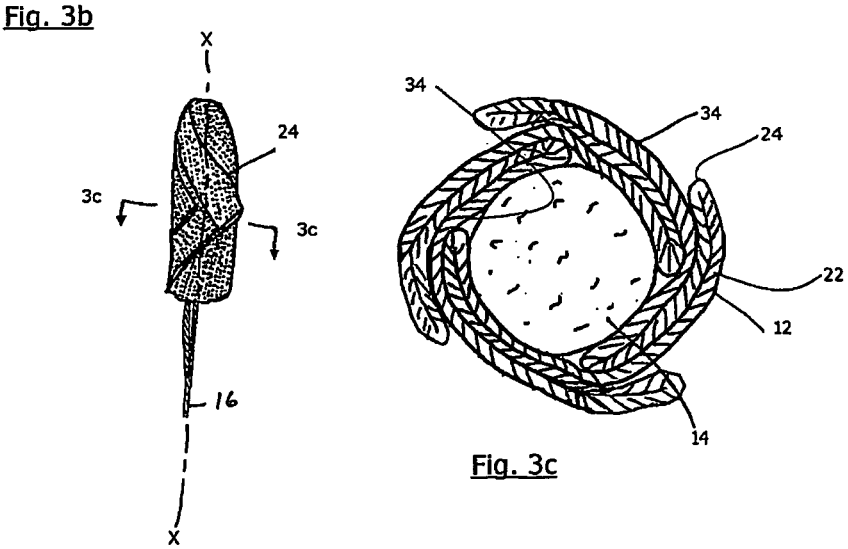
Fig. 3c

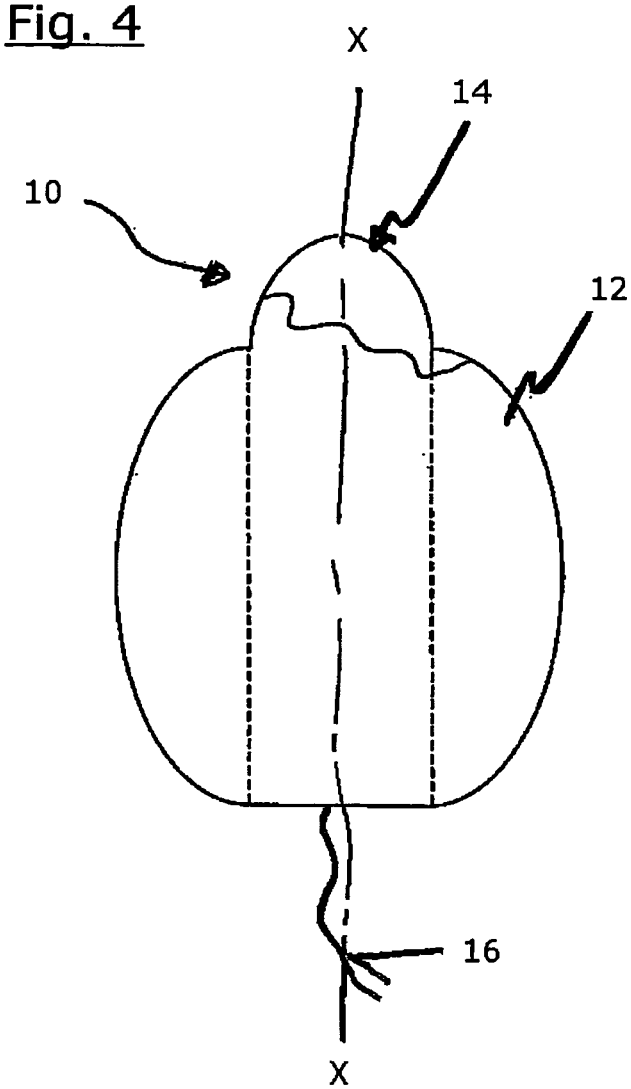

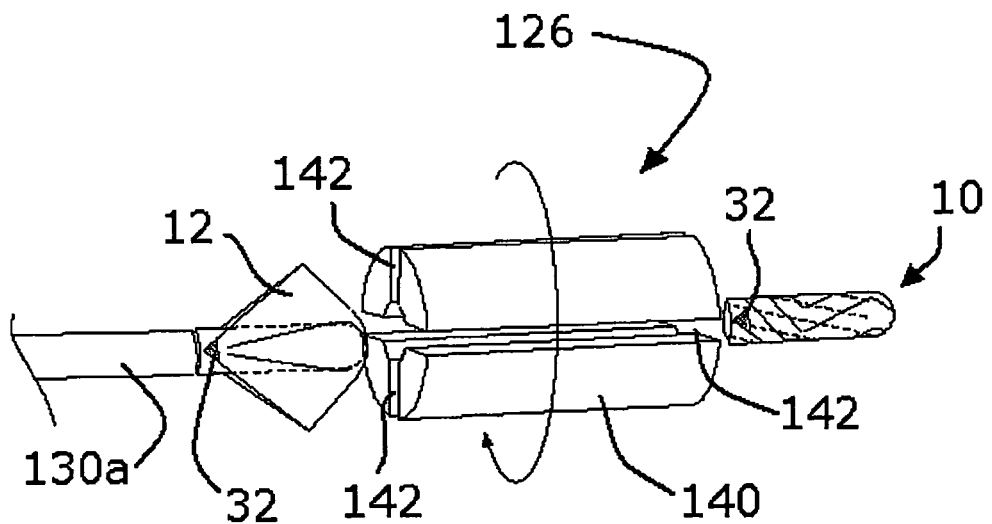
Fig. 14
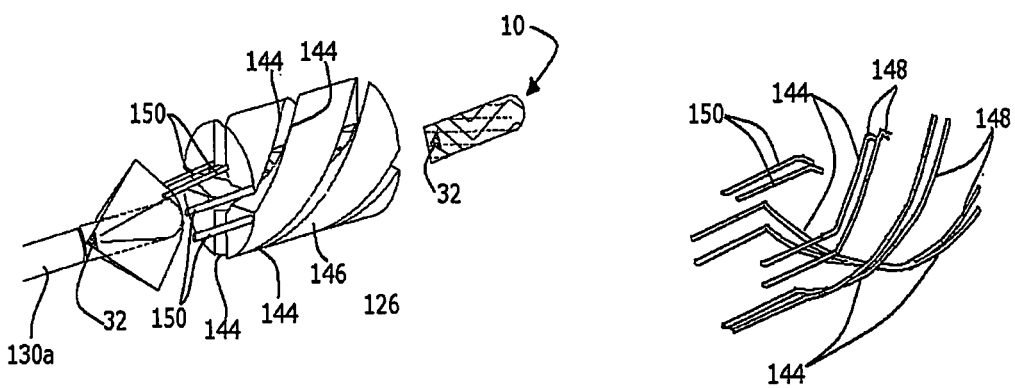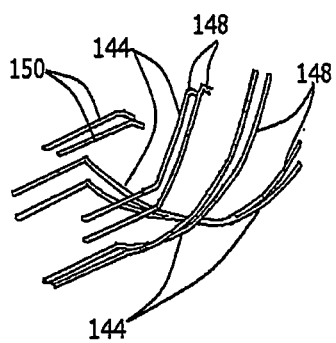
Fig. 15a  Fig. 15b

METHODS OF PACKAGING INTRAVAGINAL DEVICE

CROSS-REFERENCE TO RELATED APPLICATIONS

This application is the national stage filing under 35 USC 371 of international application PCT/US2005/018002 filed on May 16, 2005, which claims the benefit of US provisional application 60/572,054 filed on May 14, 2004, and is a continuation-in-part of US patent applications 10/847,952, filed on May 14, 2004, now U.S. Pat. No. 8,653,322, and is a continuation-in-part of US patent application 10/847,951, filed on May 14, 2004, now U.S. Pat. No. 8,247,642, and claims the benefit of US provisional application 60/572,055 filed on May 14, 2004, the complete disclosures of which are hereby incorporated herein by reference for all purposes.

This invention is also related to the following applications filed on May 14, 2004: U.S. Ser. No. 10/848,347 (US 2005/0256485A1), now abandoned, U.S. Ser. No. 10/848,257 (US 2005/0277904A1), now abandoned, and U.S. Ser. No. 10/848,208 (US 2005/0256484A1), now abandoned, the content of each of which is incorporated herein.

FIELD OF THE INVENTION

The present invention relates to devices for capturing and storing body fluid intravaginally. More particularly, the present invention relates to a method of capturing body fluid intravaginally via a fluid transport element and transporting the body fluid to a fluid storage element where the fluid is stored. Additionally, this application relates to methods of making such devices

BACKGROUND OF THE INVENTION

Devices for capturing and storing bodily fluid intravaginally are commercially available and known in the literature. Intravaginal tampons are the most common example of such devices. Commercially available tampons are generally compressed cylindrical masses of absorbent fibers that may be over-wrapped with an absorbent or nonabsorbent cover layer.

The tampon is inserted into the human vagina and retained there for a time for the purpose of capturing and storing intravaginal bodily fluids, most commonly menstrual fluid. As intravaginal bodily fluid contacts the tampon, it should be absorbed and retained by the absorbent material of the tampon. After a time, the tampon and its retained fluid is removed and disposed, and if necessary, another tampon is inserted.

A drawback often encountered with commercially available tampons is the tendency toward premature failure, which may be defined as bodily fluid leakage from the vagina while the tampon is in place, and before the tampon is completely saturated with the bodily fluid. The patent art typically describes a problem believed to occur that an unexpanded, compressed tampon is unable to immediately absorb fluid. Therefore, it presumes that premature leakage may occur when bodily fluid contacts a portion of the compressed tampon, and the fluid is not readily absorbed. The bodily fluid may bypass the tampon.

To overcome this problem of premature leakage, extra elements have been incorporated into a basic tampon to try to direct and control the flow of fluid toward the absorbent core.

For example, U.S. Pat. No. 4,212,301 (Johnson) discloses a unitary constructed digital tampon having a lower portion compressed preferably in the radial direction to form a rigid, rod-like element, which provides a central rigidified elongated core and an upper portion left substantially uncompressed. After insertion, the uncompressed portion may be manipulated to contact the vaginal wall to provide an immediate seal against side leakage. The uncompressed portion allows for high absorbent capacity immediately upon insertion. While this tampon may allow for a certain amount of protection from bypass leakage, the uncompressed portion may become saturated before the compressed portion has a chance to expand and become absorbent.

U.S. Pat. No. 6,358,235 (Osborn et al.) discloses a "hollow" bag-like tampon that may have an interior projection made from highly compressed absorbent material. The interior projection is preferably attached to the inside surface of the head of the tampon. The hollow tampon portion may include at least one pleat in the absorbent outer surface and is soft and conformable. The tampon is not pre-compressed to the point where the fibers temporarily "set" and re-expand upon the absorption of fluid. The absorbent portions of the tampon can saturate locally, which leads to bypass leakage.

U.S. Pat. No. 6,177,608 (Weinstrauch) discloses a tampon having nonwoven barrier strips that are outwardly spreadable from the tampon surface to reliably close the free spaces believed to exist within a vaginal cavity. The nonwoven barrier strips extend about the tampon in a circumferential direction at the surface or in a helical configuration about the tampon and purportedly conduct menstrual fluid toward the tampon surface. The nonwoven barrier strips are attached to the cover by means of gluing, heat bonding, needle punching, embossing or the like and form pleats. The nonwoven barrier strips are attached to the tampon blank and the blank is embossed, forming grooves extending in a longitudinal direction. While this tampon purports to direct fluid to the core, it attempts to achieve this by forming pockets of absorbent nonwoven fabric. In order to function, it appears that these pockets would have to be opened during use to allow fluid to enter. However, based upon current understandings of vaginal pressures, it is not understood how the described structure could form such an opened volume.

U.S. Pat. No. 6,206,867 (Osborn) suggests that a desirable tampon has at least a portion of which is dry expanding to cover a significant portion of the vaginal interior immediately upon deployment. To address this desire, it discloses a tampon having a compressed central absorbent core having at least one flexible extension 12 attached along a portion of the side surface of the core. The flexible extension 12 appears to provide the "dry-expanding" function, and it extends outwardly from the core away from the point of attachment. The flexible extension 12 contacts the inner surfaces of the vagina when the tampon is in place and purportedly directs fluid toward the absorbent core. The flexible extension 12 is typically attached to the pledget prior to compression of the pledget to form the absorbent core and remains in an uncompressed state.

U.S. Pat. No. 5,817,077 (Foley et al.) discloses a method of preserving natural moisture of vaginal epithelial tissue while a using a tampon where the tampon has an initial capillary suction pressure at the outer surface of less than about 40 mm Hg. This allows the tampon to absorb vaginal secretions without substantially drying the vaginal epithelial tissue. The multiple cover layers can be used to increase the thickness of the cover material. While this represents a significant advancement in the art, this invention does not address bypass leakage.

Additionally, U.S. Pat. No. 5,545,155 (Hseih et al.) discloses an external absorbent article that has a set of plates separated by spacer elements. The plates may be treated to affect wettability so that fluid will flow easily across the surface. Extending through the upper plate is a plurality of openings, which allow fluid to flow with little restriction into the space between the upper and lower plates. When the fluid flows downward in the z-direction from the upper plate to the lower plate, it will then flow laterally in the x- and y-directions. Therefore, this external absorbent article can contain fluid gushes, but it does not appear to address the problems relating in particular to intravaginal devices, such as a tampon.

While the prior art is replete with examples of sanitary protection articles that capture bodily fluids both externally and intravaginally, these examples do not overcome the problem of premature failure often identified as by-pass leakage that commonly occurs while using internal sanitary protection devices. Many solutions to this problem have involved increasing the rate of expansion of a highly compressed absorbent article.

SUMMARY OF THE INVENTION

We have found a novel way to package devices having flexible extensions. It has been discovered that imparting relative rotation and the use of helical guide rails permit effective and economical packaging of such devices.

A method of folding a plurality of flexible elements about a central fluid storage element comprising the steps of urging an intravaginal device into a folding device; imparting relative rotation between at least a portion of the folding device and the intravaginal device; and contacting the plurality of flexible extensions with the folding device. Wherein the intravaginal device includes a fluid storage element and a plurality of flexible extensions extending therefrom, and the flexible extensions are folded about the fluid storage element in a uniform direction.

A method of folding a plurality of flexible elements about a central fluid storage element comprising the steps of urging an intravaginal device into a folding device, and engaging the flexible extensions with guide rails of the folding device. The intravaginal device includes a fluid storage element and a plurality of flexible extensions extending therefrom, and the guide rails fold the flexible extensions about the fluid storage element.

Apparatus for folding a plurality of flexible elements about a central fluid storage element, the apparatus comprising a rotating element and a control rod; wherein the rotating element has a smooth inner bore and is capable of rotating with respect to a workpiece located within the inner bore, while such workpiece is held by the control rod.

Apparatus for folding a plurality of flexible elements about a central fluid storage element, the apparatus comprising a roller assembly and a control rod; wherein the roller assembly has a smooth inner bore and is capable of rotating with respect to a workpiece located within the inner bore, while such workpiece is held by the control rod.

Apparatus for folding a plurality of flexible elements about a central fluid storage element, the apparatus comprising a grooved tool and a control rod; wherein the grooved tool has a smooth inner bore and a plurality of radial slots extending from the inner bore, and the grooved tool is capable of rotating with respect to a workpiece located within the inner bore, while such workpiece is held by the control rod.

Apparatus for folding a plurality of flexible elements about a central fluid storage element, the apparatus comprising a folding tool having a feed aperture and a control rod; wherein the folding tool comprises a plurality of helical guide rails.

Other aspects and features of the present invention will become apparent to those ordinarily skilled in the art upon review of the following description of specific embodiments of the invention in conjunction with the accompanying drawings.

BRIEF DESCRIPTION OF THE DRAWING

FIGS. 3a-e show various aspects and orientations of an intravaginal device of the present invention.

FIG. 3a shows a perspective view of a tampon having a plurality of fluid transport elements extending therefrom that are formed from a folded sheet material.

FIG. 3b shows a side elevation of the tampon with a plurality of fluid transport elements wrapped around the fluid storage element.

FIG. 3c shows a transverse cross-section along line 3c-3c in FIG. 3b.

FIG. 3d shows a side elevation of the tampon of FIG. 3a.

FIG. 3e shows a top elevation of the tampon of FIG. 3a.

FIG. 4 shows a side elevation of an intravaginal device having a fluid transport element in fluid communication with a fluid storage element.

FIG. 14 shows a schematic perspective view of another alternate apparatus employing an intermittently rotating, grooved tool useful to fold flexible extensions about the fluid storage element.

FIG. 15a shows a schematic perspective view of yet another alternate stationary apparatus employing a helical tool useful to fold flexible extensions about the fluid storage element.

FIG. 15b shows a schematic perspective view of yet another alternate stationary apparatus employing helical guide rails useful to fold flexible extensions about the fluid storage element.

DETAILED DESCRIPTION OF THE PREFERRED EMBODIMENTS

As used herein in the Specification and the Claims, the term "bodily fluid" and variants thereof mean bodily exudates, especially liquids that are produced by, secreted by, emanate from, and/or discharged from a human body.

As used herein in the Specification and the Claims, the term "fluids" and variants thereof relate to liquids, and especially bodily fluids.

As used herein in the Specification and the Claims, the term "sheet" and variants thereof relates to a portion of something that is thin in comparison to its length and breadth.

As used herein in the Specification and the Claims, the term "porous medium" and variants thereof relates to a connected 3-dimensional solid matrix with a highly ramified network of pores and pore throats in which fluids may flow.

As used herein in the Specification and the Claims, the term "fluid pervious" and variants thereof relate to a material that permits fluid or moisture to pass through without additional processing, such as aperturing. Therefore, for example, an untreated woven or nonwoven material is fluid pervious and a continuous, plastic film or metal foil is not. A nonwoven permits fluid flow via the interstices between fibers, such that fluid can flow through, either by capillary action and/or via a pressure differential from one side of the nonwoven to the other such as the pressure experienced by a tampon in use.

As used herein in the Specification and the Claims, the term "in fluid communication" and variants thereof relate to elements that are arranged and configured to allow fluid to move therebetween. The fluid movement may be by interfiber capillary movement, intrafiber capillary movement, osmotic pressure, inter-plate capillary action, mechanical channeling, and the like.

As used herein in the Specification and the Claims, the term "coupled" and variants thereof relate to the relationship between two portions of an integral structure that are either portions of the same material (e.g., two portions of a folded sheet) or are materials that are joined together (e.g., two separate sheets that are bonded together).

As used herein in the Specification and the Claims, the term "fluid-permeable cover" and variants thereof relates to materials that cover or enclose surfaces of the device and reduce the ability of portions (e.g., fibers and the like) from becoming separated of the device and left behind upon removal. The term and variants thereof include, without limitation, sheet-like materials, such as apertured films and woven and non-woven fibrous webs, surface treatments, such as coatings or cover layers of integrating materials, such as binders and thermobondable fibers, and the like.

Figure 1:
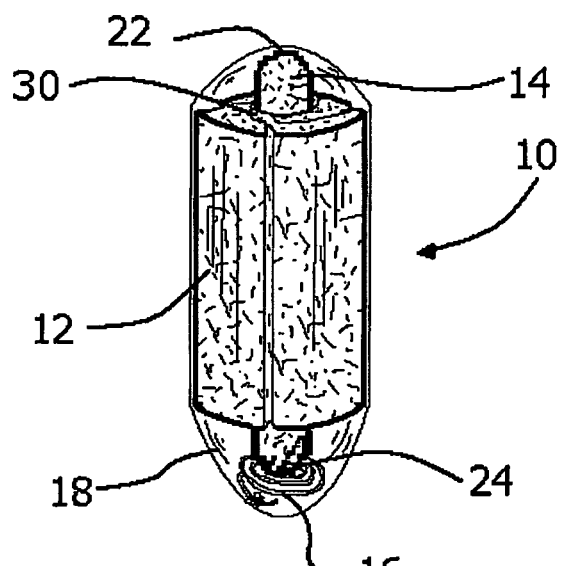
FIG. 1 is a side elevation of a packaged tampon according to the present invention.
Figure 2:
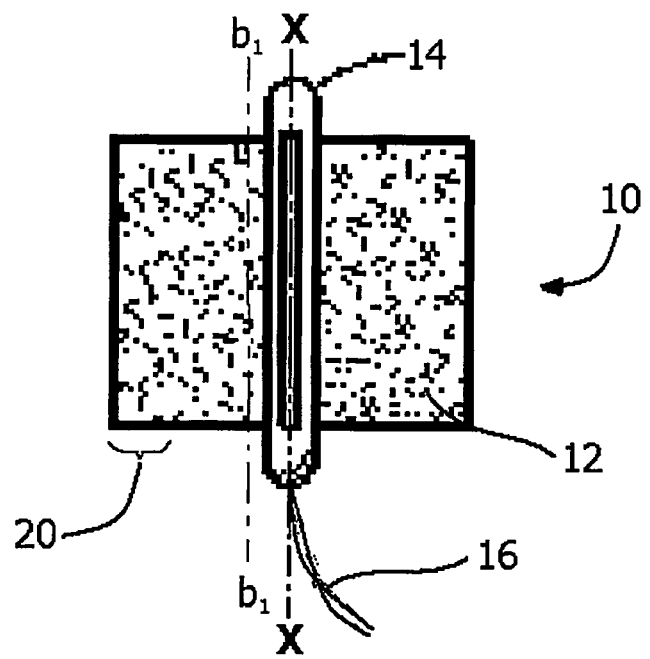
FIG. 2 is a side elevation of a tampon of the present invention with a compressed absorbent core and flexible panels extending therefrom.

Referring to FIG. 1, one embodiment of this invention provides a packaged intravaginal device 10 having at least one flexible extension 12 connected to with a fluid storage element 14 (FIG. 1 shows a plurality of flexible extensions 12 located about and extending from sides of the fluid storage element 14). The intravaginal device 10 may also include a withdrawal mechanism, such as a string 16. The flexible extensions 12 are shown wrapped around the fluid storage element 14. The extensions are maintained in this configuration by hygienic overwrap 18. However, as shown in FIG. 2, a distal portion 20 of the flexible extensions 12 may extend radially away from the fluid storage element 14 during use.

The fluid storage element 14 can be any convenient shape including cylindrical, cup like, hourglass, spherical, etc. It can be an absorbent or a fluid collection device. It can be in separate sections with the fluid transport element(s) bridging or connecting the sections. The fluid storage element 14 can be made of any structure known in the art, such as compressed fibrous webs, rolled goods, foam, and the like. The material may be formed as a unitary mass or a plurality of discrete particles or agglomerations. The material may be compressed to maintain a relatively stable form, or it may be left relatively uncompressed. For example, the absorbent material may include a central portion of absorbent wood pulp material. The pulp may be covered by a thin absorbent woven or nonwoven fabric and may be coterminous with the fluff pad or completely envelop it on all sides. Absorbent materials that are uncompressed or of low density have a much higher holding capacity for fluids than high-density materials. A consideration for using uncompressed materials is the bulk or volume that may be required in order to achieve sufficient absorbency.

In one preferred embodiment, the fluid storage element 14 is an absorbent tampon. Absorbent tampons are usually substantially cylindrical masses of compressed absorbent material having a central axis and a radius that defines the outer circumferential surface of the tampon. Such tampons are disclosed in e.g., Haas, U.S. Pat. No. 1,926,900; Dostal, U.S. Pat. No. 3,811,445; Wolff, U.S. Pat. No. 3,422,496; Friese et al., U.S. Pat. No. 6,310,296; Leutwyler et al., U.S. Pat. No. 5,911,712, Truman, U.S. Pat. No. 3,983,875; Agyapong et al., U.S. Pat. No. 6,554,814. Tampons also usually include a fluid-permeable cover (which may include or be replaced by another surface treatment) and a withdrawal string or other removal mechanism.

Absorbent materials useful in the formation of the fluid storage element 14 include fiber, foam, superabsorbent, hydrogels, and the like. Preferred absorbent material for the present invention includes foam and fiber. Absorbent foams may include hydrophilic foams, foams that are readily wetted by aqueous fluids as well as foams in which the cell walls that form the foam themselves absorb fluid.

Fibers may be selected from cellulosic fiber, including natural fibers (such as cotton, wood pulp, jute, and the like) and synthetic fibers (such as regenerated cellulose, cellulose nitrate, cellulose acetate, rayon, polyester, polyvinyl alcohol, polyolefin, polyamine, polyamide, polyacrylonitrile, and the like).

The fluid storage element 14 may also be in the form of a collection cup. Examples of such devices are disclosed in Zoller, U.S. Pat. No. 3,845,766 and Contente et al., U.S. Pat. No. 5,295,984. Collection devices are designed to assume a normally open, concave configuration, with an open side facing a user's cervix. The collection devices may be folded, or otherwise manipulated, to facilitate insertion into the vaginal canal.

The flexible extensions 12 can be made of almost any hydrophobic or hydrophilic material, preferably a sheet-like web. For example, the extension(s) 12 may be constructed from a wide variety of liquid-absorbing or liquid-transporting materials commonly used in absorbent articles such as rayon, cotton, or comminuted wood pulp which is generally referred to as airfelt. Examples of other suitable absorbent materials include creped cellulose wadding; meltblown polymers including conform; chemically stiffened, modified or cross-linked cellulosic fibers; synthetic fibers such as crimped polyester fibers; peat moss; tissue including tissue wraps and tissue laminates; or any equivalent material or combinations of materials, or mixtures of these. In addition, materials useful for forming the flexible extension 12 may have properties such as thermobondability to provide means to incorporate it into the intravaginal device 10. A representative, non-limiting list of useful materials includes polyolefins, such as polypropylene and polyethylene; polyolefin copolymers, such as ethylenevinyl acetate ("EVA"), ethylene-propylene, ethylene-acrylates, and ethylene-acrylic acid and salts thereof; halogenated polymers; polyesters and polyester copolymers; polyamides and polyamide copolymers; polyurethanes and polyurethane copolymers; polystyrenes and polystyrene copolymers; and the like. The extension(s) 12 and any component thereof may comprise a single material or a combination of materials.

The thickness of each extension is not critical. However, it can preferably be selected from the range of from about 0.005 to about 0.250 inch. Preferably, the materials of construction and the thickness of the extensions are designed to be sufficiently stiff and/or resistant to wet collapse when exposed to fluid.

The flexible extension 12 should be strong enough to prevent rupturing during handling, insertion, and removal and to withstand vaginal pressures during use.

It is preferable that the flexible extension(s) 12 are sufficiently wettable by the bodily fluids that the intravaginal device 10 is intended to collect (this results largely from a correlation of the surface energy of the extension surface and the bodily fluid(s)). Thus, the bodily fluid will easily wet the extension, and a driving mechanism can divert fluid toward the fluid storage element 14. In particularly preferred embodiments, this driving mechanism is provided though the use of capillary channel fibers, an osmotic driving force, a hydrophilicity gradient, a capillary driving force, or some combination of these.

Surface treatments can be used to modify the surface energy of the extension(s) 12. In a preferred embodiment a surfactant is applied to increase the wettability of the extension(s) 12. This will increase the rate at which the bodily fluids are drawn into and transported by a flexible extension 12. The surfactant can be applied uniformly, or it can be applied with varying coating weights in different regions.

A useful measure to determine the wettability of an extension material is its contact angle with 1.0% saline. Preferably, the contact angle with 1.0% saline is less than about 90 degrees.

In order to accomplish this, the materials of extension(s) can be chosen from those materials that are known in the art to have low energy surfaces. It is also possible and useful to coat materials with high-energy surfaces with a surface additive, such as a non-ionic surfactant (e.g., ethoxylates), a diol, or mixtures thereof, in order to increase their wettability by bodily fluids. Such additives are well known in the art, and examples include those described in Yang et al., U.S. App. No. 2002-0123731-A1, and U.S. Pat. No. 6,570,055. Other means of increasing wettability can also be used, such as blending in hydrophilic fibers, etc.

The flexible extension 12 can be of any flexibility as long as the material is able to transport fluid to the fluid storage element 14 while the device is in use. It is also preferable that the flexible extension 12 be sufficiently flexible to provide the user with comfort while inserting, wearing, and removing the device.

Figure 3D:
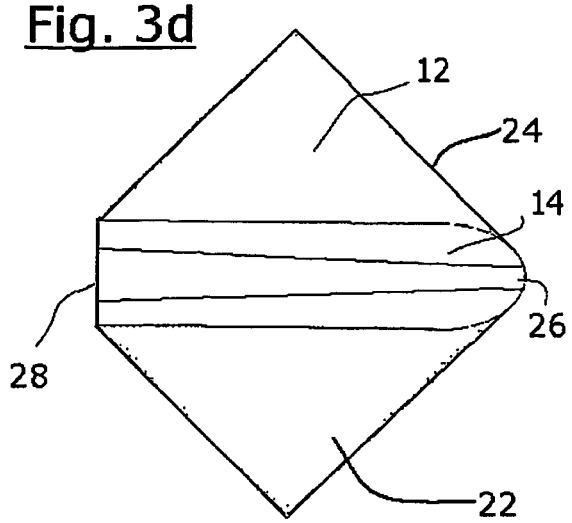
Figure 3E:
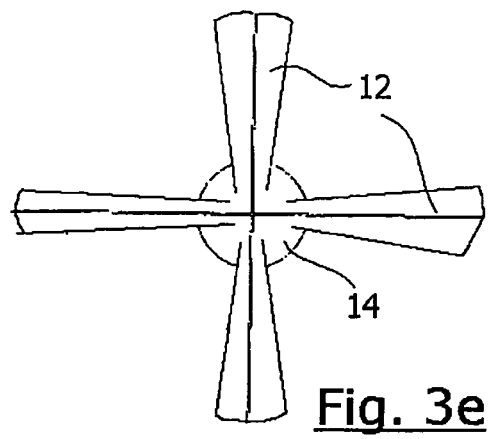

An embodiment with extensions formed by folding the cover material 22 into pleats 24 is shown in FIGS. 3a-3e. The extensions are bendable about an infinite number of bending axes ($b_{1-i}$-$b_{1-i}$) that are substantially parallel to the longitudinal axis (X-X) of the product, which longitudinal axis extends through the insertion end 26 and withdrawal end 28. These bending axes allow the extensions to wrap around the product, either partially or completely. One such bending axis ($b_1$-$b_1$) is shown in FIG. 3a.

The flexible extension 12 may be arranged and configured to direct bodily fluid from the body cavity to the storage element 14. Generally, fluid will be directed from each flexible extension 12 to a particular region of the fluid storage element 14 associated with that flexible extension 12. Thus, if the device has only one flexible extension 12, the fluid will contact the fluid storage element 14 in one interface 30.

Therefore, additional flexible extension 12 directing fluid to additional locations of the fluid storage element 14 will improve the efficient usage of the fluid storage element 14. For example, two flexible extensions 12 could be directed to opposite sides of the fluid storage element 14, as shown in FIG. 4. Each additional flexible extension 12 can direct fluid to additional interface locations 30 of the fluid storage element 14. For example, four evenly spaced flexible extensions 12 allow fluid to be directed to each quarter of the fluid storage element 14 surface as shown in FIGS. 3a-e. Five or more elements would provide even more direct access. This can allow the fluid to contact the fluid storage element 14 uniformly and help to prevent or reduce local saturation of the fluid storage element 14.

Enlarging the area of the interface 30 between the flexible extension 12 and fluid storage element 14 can also help to maximize the fluid communication. For example, elongating the interface by increasing the length of the flexible extension 12 allows more fluid to flow into the fluid storage element 14.

While the above description provides for direct fluid communication between a flexible extension 12 and the fluid storage element 14, direct fluid contact is not necessary and may not even be necessary. This depends upon the desired use. There can also be fluid communication through an intermediate element, such as a porous medium (e.g., a foam or fibrous structure), a hollow tube, and the like. Thus, the flexible extension(s) 12 may be indirectly secured to the other element by affixing the element to intermediate member(s), which intermediate member(s) in turn are affixed to the other element; and configurations in which one element is integral with another element; i.e., one element is essentially part of the other element.

The flexible extension 12 may be formed to extend from the surface of the fluid storage element 14 as in FIGS. 2-4. It can be made in any convenient shape, including semicircular, triangular, square, hourglass etc.

The flexible extensions 12 may be joined, directly or indirectly, to the fluid storage element 14 by any variety of means. A representative, non-limiting list of useful means include heat, adhesive, ultrasonic, sewing, and mechanically engaging the fluid storage element 14. An example of a heat-bonded attachment 32 is shown in FIG. 3a. The joining of the flexible extensions 12 may take the form of a single attachment 32 or one or more groupings of attachments in an attachment zone.

The flexible extension(s) 12 can be attached at the sides, insertion end 26, and/or withdrawal end 28 of the intravaginal device 10. Additionally, the flexible extension(s) 12 may be attached to themselves and not to the storage element 14 as in a bag type covering of the storage element 14. The flexible extensions 12 could also be attached to the withdrawal string. These and other means of attachment are disclosed in the commonly-assigned, copending patent applications entitled "Intravaginal Device with Fluid Acquisition Plates" (U.S. Ser. No. 60/574,054), "Intravaginal Device with Fluid Acquisition Plates and Method of Making" (U.S. Ser. No. 60/572,055), both filed on even date herewith, the contents of which are herein incorporated by reference.

Figure 5:
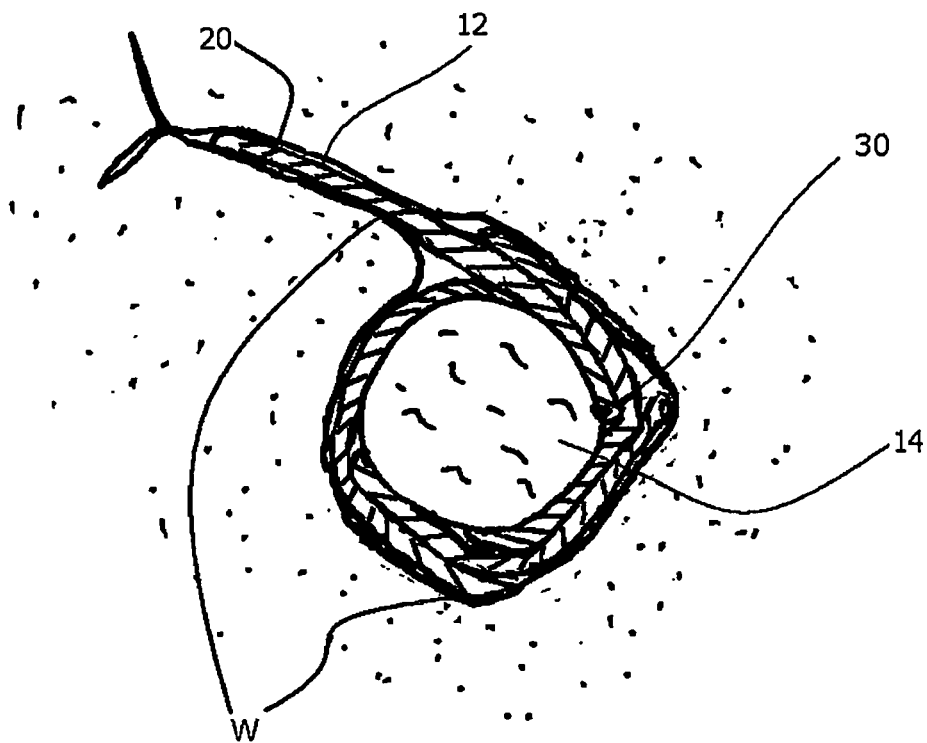
FIG. 5 shows a transverse cross-section of a human vagina with an intravaginal device according to FIG. 3b disposed therein with one fluid transport element extending away from the fluid storage element.
Figure 6:
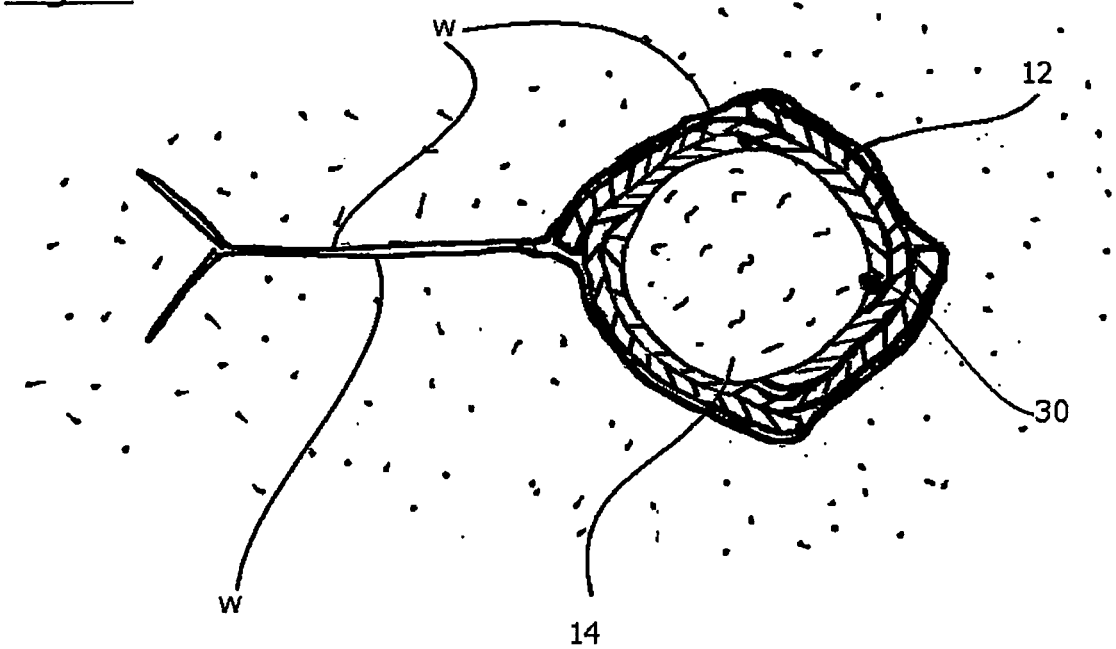
FIG. 6 shows a transverse cross-section of a human vagina with an intravaginal device according to FIG. 3b disposed therein with the fluid transport elements remaining wrapped around the fluid storage element.

During use, flexible extension(s) 12 can take on many configurations within the vagina. For example, a distal portion 20 of the flexible extension 12 may extend into the vagina away from the fluid storage element 14, as shown in FIG. 5. Alternatively, and the flexible extension(s) 12 may remain wound about the fluid storage element 14, contacting the vaginal wall "W" only through a major surface 34 (FIG. 6).

The major surface 34 of the flexible extension 12 or extensions may be plain, or it can be textured. It is also acceptable in embodiments with multiple extensions 12 to have both textured and non-textured extensions.

A fluid-permeable cover 36 may substantially enclose the fluid storage element 14. The fluid-permeable cover may also enclose the major surfaces 34 of the flexible extension(s) 12. Thus, the cover 36 encloses a majority of the outer surface of the tampon. In addition, the cover may enclose either or both ends of the tampon. Of course, for processing or other reasons, some portions of the surface of the tampon may be free of the cover. For example, the insertion end 26 of the tampon and a portion of the cylindrical surface adjacent this end may be exposed, without the cover to allow the tampon to more readily accept fluids. Additionally, the edges 38 of the flexible extension(s) 12 may also be exposed.

The fluid-permeable cover 36 can ease the insertion of the tampon into the body cavity and can reduce the possibility of fibers being separated from the tampon. Useful covers are known to those of ordinary skill in the art. They may be selected from an outer layer of fibers that are fused together (such as by thermobonding), a nonwoven fabric, an apertured film, or the like. Preferably, the cover has a hydrophobic finish.

Tampons are generally categorized in two classes: applicator tampons and digital tampons, and a certain amount of dimensional stability is useful for each type of tampon. Applicator tampons use a relatively rigid device to contain and protect the tampon prior to use. To insert the tampon into a body cavity, the applicator containing the tampon is partially inserted into the body cavity, and the tampon can be expelled from the applicator into the body cavity. In contrast, digital tampons do not have an applicator to help guide them into the body cavity and require sufficient column strength to allow insertion without using an applicator.

While the applicator tampon is protected by the rigid applicator device and the applicator tampon need not as have as high a degree of column strength as a digital tampon, applicator tampons do require dimensional stability (especially radial) to be acceptable for use. This dimensional stability provides assurance, for example, that the tampon will not prematurely grow and split the packaging material or become wedged in a tampon applicator.

Figure 7:
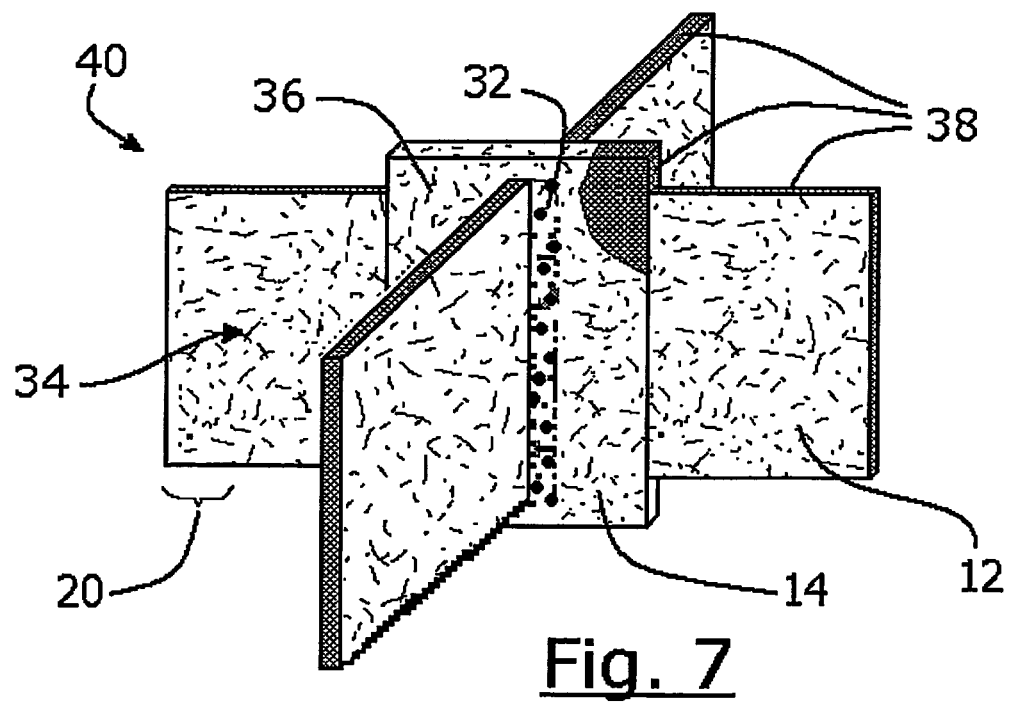
FIG. 7 is a side elevation of a tampon of the present invention prior to the compression of an intermediate structure.
Figure 8:
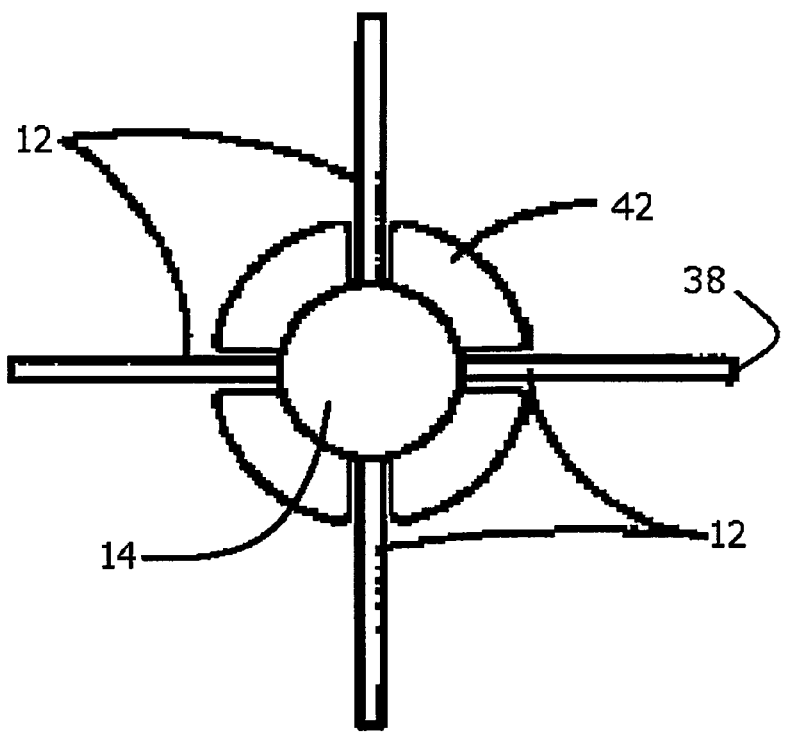
FIG. 8 is a top view showing one manner in which the intermediate structure of the tampon of the present invention may be compressed.

To form a tampon ready for use, an intermediate structure 40 (e.g., as shown in FIG. 7) is typically compressed and heat conditioned in any suitable conventional manner. Pressures and temperatures suitable for this purpose are well known in the art. Typically, the intermediate structure 40 is compressed in both the radial and axial direction using any means well known in the art. While a variety of techniques are known and acceptable for these purposes, a modified tampon compressor machine available from Hauni Machines, Richmond, Va., is suitable. Preferably, the flexible extensions 12 are attached to the intermediate structure 40 as shown in FIG. 7. The intermediate structure 40 may then be compressed to form the fluid storage element 14 as shown in FIG. 8. FIG. 8 shows a series of compression dies 42 provided with narrow axial slits, which allow compression of the fluid storage element 14 without compressing the flexible extensions 12. It may also be desirable in some embodiments to attach the flexible extensions 12 to the fluid storage element 14 after compression of such element.

Figure 9:
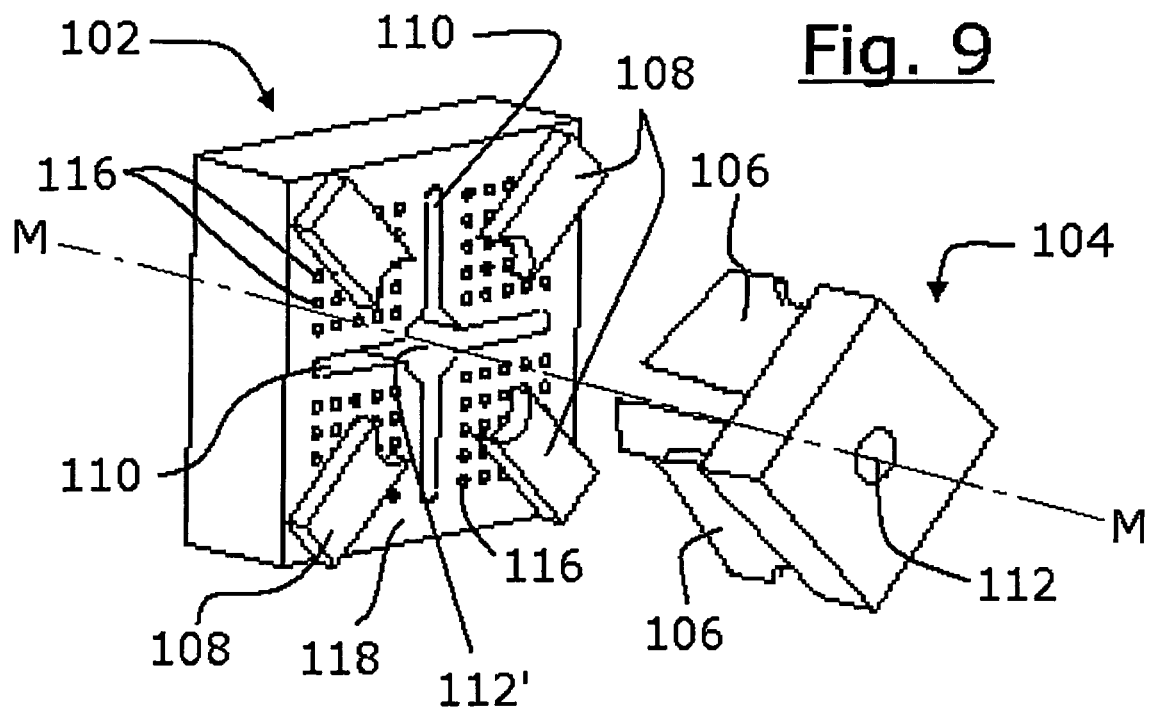
FIG. 9 shows a schematic perspective view of apparatus according to the present invention useful to manufacture an intravaginal device.
Figure 10:
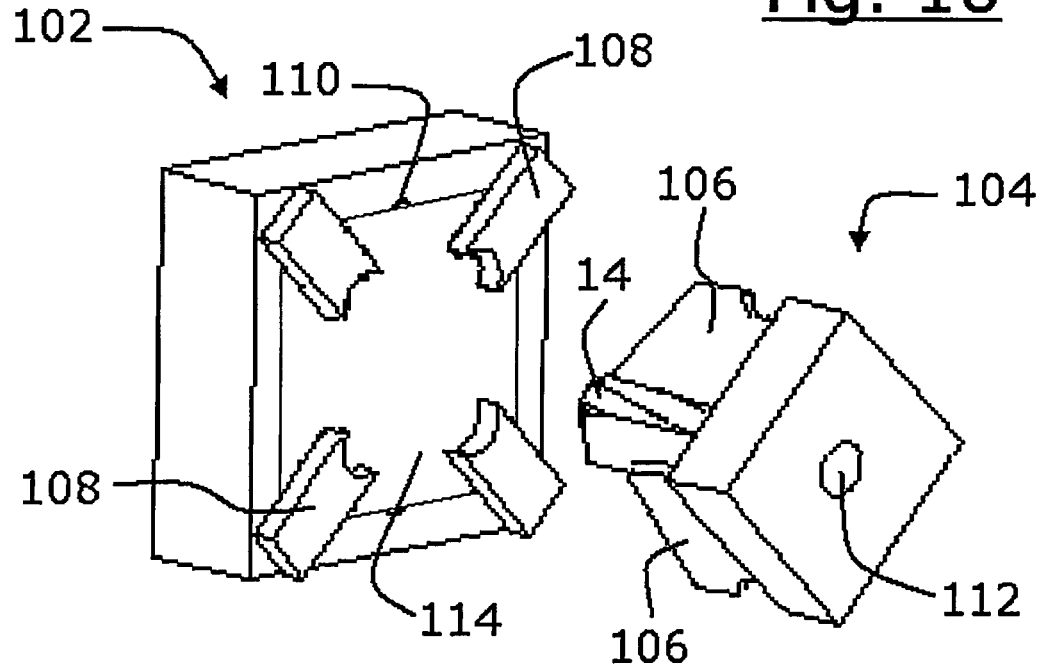
FIG. 10 shows the schematic perspective view of apparatus of FIG. 9 including a fluid storage element and a sheet of material prior to formation of the fluid transport element.

As previously mentioned and shown, the fluid transport element 12 may be attached to the fluid storage element 14 be any number of methods and embodiments. For example and with reference to FIGS. 9-11, a tampon may be manufactured as shown in Friese, U.S. Pat. No. 4,816,100, and either Friese et al., U.S. Pat. No. 6,310,269, or Leutwyler et al., U.S. Pat. No. 5,911,712. However, after the tampon is formed and prior to packaging, an additional process employing a forming tool 102, a male tool 104 having a plurality of blades 106, and thermobonding elements 108 applies a fluid transport element 12 to the fluid storage element 14. The tools are aligned in a manner that the blades 106 of the male tool 104 cooperate with corresponding slots 110 in the female tool 102. In addition, each of the tools has a central aperture 112, 112' through which a fluid storage element 14 may pass during processing.

In somewhat more detail, an individual sheet 114 of material is separated from a supply (not shown) and placed on the forming tool 102. A vacuum is drawn across the forming tool 102 via a plurality of vacuum ports 116 on the face 118 of the forming tool 102 to hold the individual sheet 114 in place.

Figure 11:
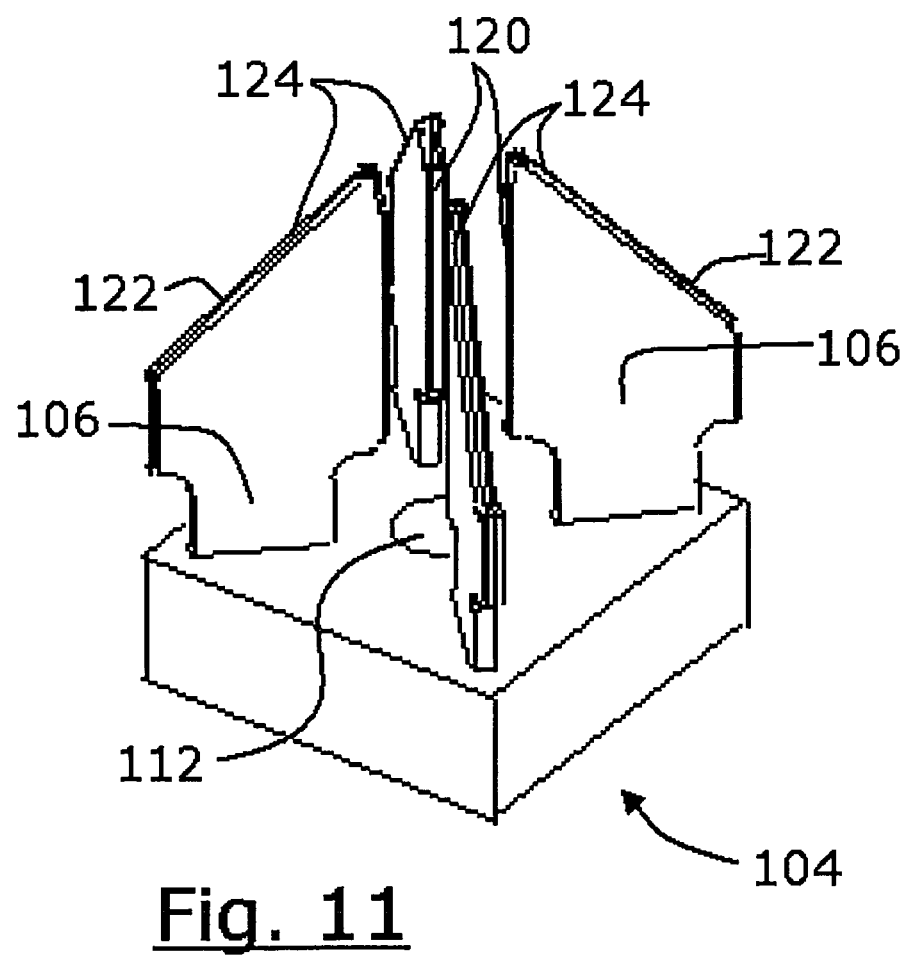
FIG. 11 shows a schematic perspective view of a male tool useful in the apparatus of FIG. 9.

The blades 106 of the male tool 104 are shown arranged radially about the central aperture 112 in the male tool 104 (as shown in FIG. 11). The blades 106 cooperate to hold the fluid storage element 14 in line with the central aperture 112. A pushrod (not shown) is arranged to penetrate the central aperture 112 of the male tool 104 and to bear on the base of the fluid storage element 14. In the preferred embodiment shown in FIGS. 9-11, four blades 106 are arranged at equal angles about the central aperture 112. Each blade 106 provides a guide edge 120 facing the fluid storage element 14 (when present) and a pleating edge 122 disposed radially outwards from the guide edge 120. The pleating edge 122 may be an edge that is adjacent the guide edge 120, or it may be separated by one or ore intermediate portions of the blade 106.

In operation, the male tool 104 holding a fluid storage element 14 is moved along the machine axis (M-M) aligned with the central apertures 112, 112' toward the forming tool 102 carrying the individual sheet 114. The insertion end 26 of the fluid storage element 14 contacts the individual sheet 114 and urges it through the central aperture 112' of the forming tool 102. The pleating edges 112 of the blades 106 urge corresponding portions of the individual sheet 114 through the slots 110 of the forming tool 102.

Once the fluid storage element 14 is inserted into the central aperture 112' of the forming tool 102 with only a portion of the withdrawal end 28 remaining exposed, thermobonding elements 108 extend into the space between the blades 106 to bond the four corners of the individual sheet 110 to the exterior surface 62 of the fluid storage element 14, forming the fluid transport element 12. The pushrod may then continue to move the insertable device 10 into and through the central aperture 112' of the forming tool 102.

While the process described above in reference to FIGS. 9-11 employs blades 106 that have a guide edge 120 that is shorter than the fluid storage element 14, this relationship may be altered. For example, the blades 106 could be modified to have a guide edge 120 that is longer than the fluid storage element 14 or the system could otherwise be modified to allow the leading portions 124 to contact the individual sheet 114, first. This permits the formation of a small gap between the insertion end 48 of the tampon and the individual sheet 114 that may allow more free expansion of the tampon without restriction by the fluid transport element 14 during use.

The fluid transport element 12 may then be folded about the fluid storage element 14. According to the present invention, the transport element is folded by urging the intravaginal device 10 through one or more folding device(s) in which there is relative rotation between the folding device and the intravaginal device 10. Alternatively, the intravaginal device 10 may pass through a stationary device having guide rails that fold the flexible extensions 12 about the fluid storage element 14.

Figure 12:
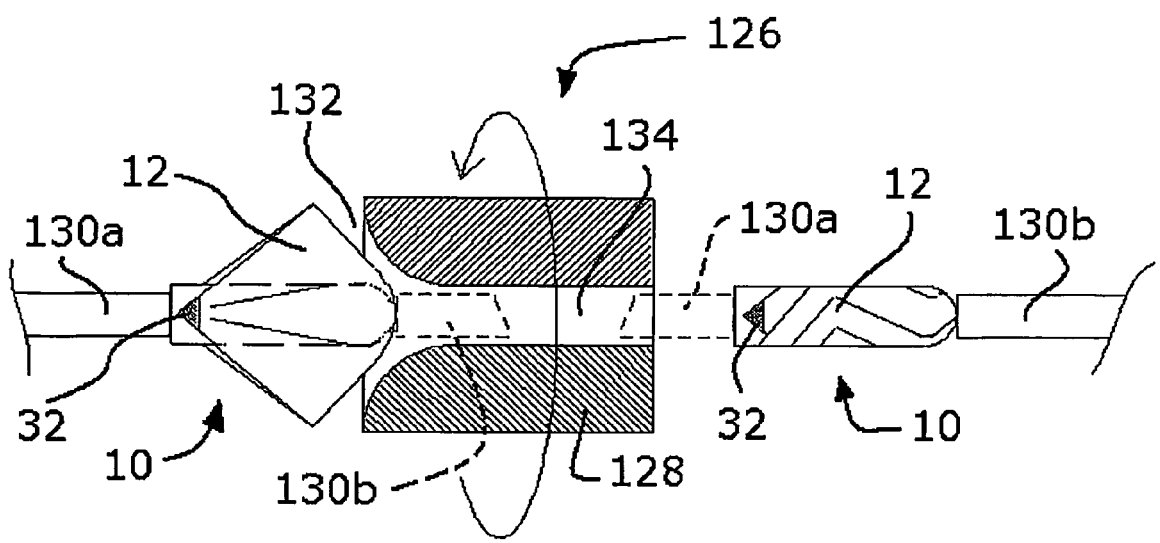
FIG. 12 shows a schematic longitudinal cross-section of apparatus employing a smooth spinning funnel useful to fold flexible extensions about the fluid storage element.

In a first embodiment, shown in FIG. 12, the folding tool 126 comprises a rotating element, such as a smooth spinning funnel 128 provides the rotation as a pair of control rods 130a and 130b moves the intravaginal device 10 through it. The feed aperture 132 is appropriately radiused, depending upon the size of the intravaginal device 10. The smooth inner bore 134 of the spinning funnel 128 folds the flexible extensions about the fluid storage element 14 without damage.

Figure 13:
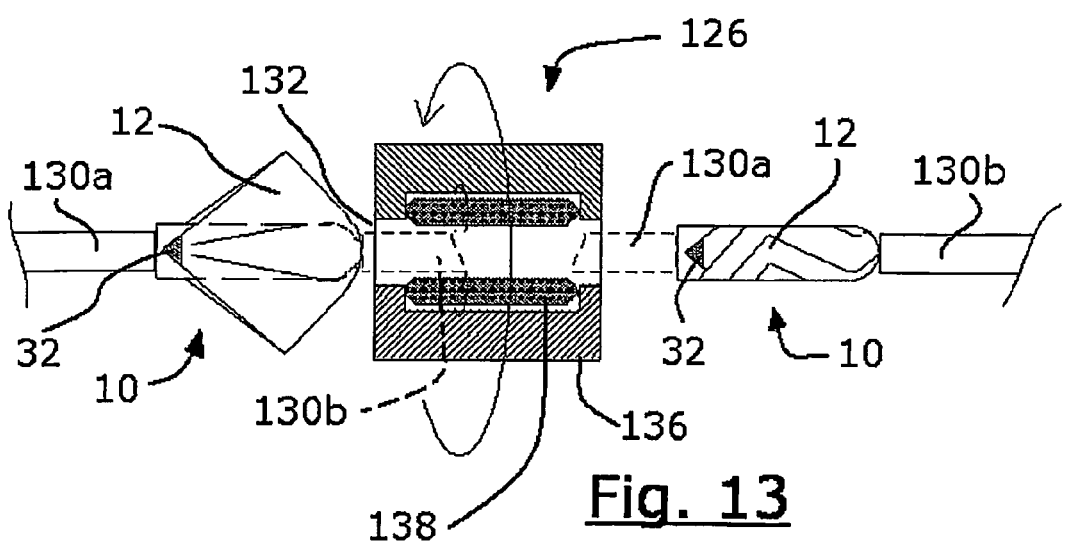
FIG. 13 shows a schematic longitudinal cross-section of an alternate apparatus employing a rotating roller assembly useful to fold flexible extensions about the fluid storage element.

In a second embodiment, shown in FIG. 13, the folding tool 126 comprises a rotating roller assembly 136 in place of the spinning funnel 128. Again, a pair of control rods 130a and 130b moves the intravaginal device 10 through the rotating roller assembly 136, and the feed aperture 132 is appropriately radiused. In this embodiment, a plurality of roller bearings 138 disposed about the inner bore 134 of the spinning roller assembly 136 folds the flexible extensions about the fluid storage element 14 without damage.

In the embodiments of FIGS. 12 and 13, the folding tool may rotate intermittently or continuously. Preferably, the tool rotates continuously at about 500 to about 5,000 rotations per minute ("rpm"), preferably about 600 to about 1,000 rpm. Alternately, about 2,000 to about 3,000 rpm. If the rotation is too slow, the extensions may become wrinkled. If it is too fast, the extensions may be torn or melted, if the friction is too great.

In a third embodiment, shown in FIG. 14, the folding tool 126 comprises a grooved tool 140. While the embodiments of FIGS. 12 and 13, above may rotate intermittently or continuously, the grooved tool 140 preferably rotates only intermittently. For example, pair of control rods 130a and 130b moves the intravaginal device 10 into the stationary grooved tool 140 while the flexible extensions 12 are aligned with corresponding grooves 142 disposed in the grooved tool 140. The grooved tool 140 then rotates to a degree necessary to fold the flexible extensions 12 about the fluid storage element 14, for example about 180°, and then stops rotating. The control rods 130a and 130b then move the intravaginal device 10 to the next processing station. Of course, in any of the embodiments of FIGS. 12-14, it is only necessary for relative rotation between the folding tool 126 and the intravaginal device 10. While the above description has discussed processes in which the folding tool 126 rotates, one of ordinary skill in the art will recognize that the folding tool 126 may remain stationary, while the control rods 130a and 130b impart rotation to the intravaginal device 10.

In a fourth embodiment, shown in FIGS. 15a and b, the folding tool 126 comprises a plurality of helical guide rails 144. These guide rails 144 may be integral portions of an appropriately formed helical tool 146, or they may be individual rails 148 (as shown in FIG. 15b) combined to provide the appropriate folding of the flexible extensions 12. Again, a pair of control rods 130a and 130b moves the intravaginal device 10 through the folding tool 126. It is preferred that a set of substantially straight feed rails 150 leads into the helical rails 144 to provide a controlled introduction of the flexible extensions 12 into the helical rails. The helical rails 144 guide each flexible extension 12 through the folding tool 126 into a smoothly folded configuration about the fluid storage element 14.

Once the flexible extensions 12 are folded about the fluid storage element 14, the insertable device 10 may then be packaged in a hygienic overwrap 18 in any manner that may be recognized by those skilled in the art.

The intravaginal device 10 of the present invention may be inserted digitally or through the use of an applicator. If the intravaginal device 10 is to be used for digital insertion, it may be desirable to form the pledget from a layer of absorbent material that has been rolled into a cylindrical shape. Flexible extensions 12 could be attached to such a layer in any suitable manner. For example, the attachment 32 shown in FIG. 7 may be used to attach one or more flexible extensions 12 to an intermediate structure 40.

Figures 16, 17:
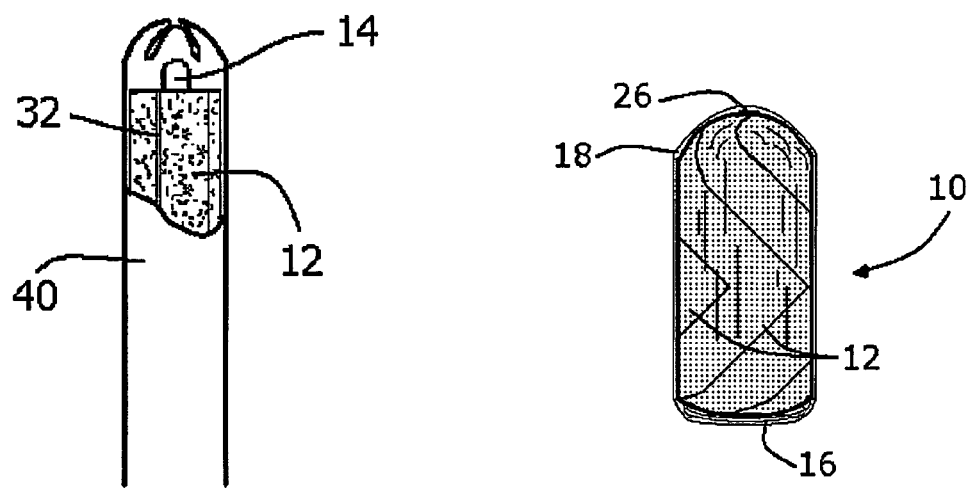
FIG. 16 is a partially cut-away side elevation of a tampon of the present invention within an applicator.
FIG. 17 is a side elevation of a alternate packaged tampon according to the present invention.

Any of the currently available tampon applicators may also be used for insertion of the tampon of the present invention. Such applicators of typically a "tube and plunger" type arrangement and may be plastic, paper, or other suitable material. Additionally, a "compact" type applicator is also suitable. The flexible nature of the flexible extensions 12 allows them to reside in the applicator tube 152 as shown in FIG. 16. The applicator plunger will push the intravaginal device 10 out of the applicator 152 due to the compressed nature of the product. The flexible extensions 12 are then available to begin collecting fluid immediately after insertion from their generally uncompressed state.

A withdrawal mechanism, such as withdrawal string 16, is preferably joined to the intravaginal device 10 for removal after use. The withdrawal mechanism is preferably joined to at least the fluid storage element 14 and extends beyond at least its withdrawal end 28. Any of the withdrawal strings currently known in the art may be used as a suitable withdrawal mechanism, including without limitation, braided (or twisted) cord, yarn, etc. In addition, the withdrawal mechanism can take on other forms such as a ribbon, loop, tab, or the like (including combinations of currently used mechanisms and these other forms). For example, several ribbons may be twisted or braided to provide flexible extensions structures.

Further, the intravaginal device 10 can be collapsed for packaging and insertion. For example, at least a portion of a major surface 34 of the flexible extension 12 may be in contact with at least a portion of an outer surface 154 of the fluid storage element 14. This can be achieved by wrapping the flexible extension(s) 12 around the fluid storage element 14. The thus-compacted device can then be packaged, (e.g., within an applicator 152 (FIG. 16) or alone in a hygienic overwrap 18 (FIG. 17)).

The specification and embodiments above are presented to aid in the complete and non-limiting understanding of the invention disclosed herein. Since many variations and embodiments of the invention can be made without departing from its spirit and scope, the invention resides in the claims hereinafter appended.

What is claimed is:

1. A method of folding a plurality of flexible elements about a central fluid storage element comprising the steps of:
   a. urging an intravaginal device comprising a fluid storage element which comprises a substantially cylindrical mass of compressed absorbent material having a fluid-permeable cover disposed about an outer circumferential surface of the substantially cylindrical mass of compressed absorbent material and a plurality of sheet-like flexible extensions attached by at least one attachment to the cover of the fluid storage element, the sheet-like flexible extensions having a thickness of about 0.005 to about 0.25 inches extending therefrom into a folding device;

b. imparting relative rotation between at least a portion of the folding device and the intravaginal device; and c. contacting the plurality of flexible extensions with the folding device thereby folding the flexible extensions about the fluid storage element in a uniform direction.

2. The method of claim 1, wherein the folding device comprises a rotating element having an inner bore defined along its axis of rotation.

3. The method of claim 2, wherein the rotating element comprises a cylinder centered on the axis of rotation.

4. The method of claim 2, wherein a feed aperture is enlarged with respect to the inner bore.

5. The method of claim 2, wherein the inner bore is substantially smooth.

6. The method of claim 2, wherein the inner bore has a plurality of roller bearings disposed thereabout.

7. The method of claim 2, wherein the inner bore has a plurality of radial slots extending therefrom.

8. The method of claim 7, wherein the number of slots corresponds to the number of flexible extensions on the intravaginal device.

9. The method of claim 2, wherein the rotating element rotates substantially continuously.

10. The method of claim 9, wherein the rotating element rotates at about 600 to about 1,000 revolutions per minute ("rpm").

11. The method of claim 2, wherein the rotating element rotates substantially intermittently.

12. The method of claim 11, wherein the rotating element rotates in a reciprocating manner.

13. The method of claim 11, wherein the rotating element rotates in a single rotational direction.

14. The method of claim 1, wherein the folding device folds each flexible element through an angle of at least 180 degrees.

15. The method of claim 1, wherein the at least one attachment of the extensions is located at the side of the fluid storage element.

16. The method of claim 1, wherein the at least one attachment of the extensions is located proximate the insertion end of the fluid storage element.

17. The method of claim 1, wherein the at least one attachment of the extensions is located proximate the withdrawal end of the fluid storage element.

* * * * *